United States Patent
Saito

(10) Patent No.: US 11,591,384 B2
(45) Date of Patent: Feb. 28, 2023

(54) **IMMUNOLOGICAL DETECTION METHOD AND KIT FOR *MYCOPLASMA PNEUMONIAE***

(71) Applicant: TAUNS CO., LTD., Izunokuni (JP)

(72) Inventor: Kenji Saito, Izunokuni (JP)

(73) Assignee: TAUNS CO., LTD., Shizuoka (JP)

( * ) Notice: Subject to any disclaimer, the term of this patent is extended or adjusted under 35 U.S.C. 154(b) by 0 days.

(21) Appl. No.: 15/547,346

(22) PCT Filed: Jan. 27, 2016

(86) PCT No.: PCT/JP2016/052381
§ 371 (c)(1),
(2) Date: Jul. 28, 2017

(87) PCT Pub. No.: WO2016/121831
PCT Pub. Date: Aug. 4, 2016

(65) Prior Publication Data
US 2018/0009880 A1    Jan. 11, 2018

(30) Foreign Application Priority Data
Jan. 29, 2015 (JP) .............................. JP2015-015253

(51) Int. Cl.
*C07K 16/12* (2006.01)
*C12N 15/09* (2006.01)
(Continued)

(52) U.S. Cl.
CPC .......... *C07K 16/1253* (2013.01); *C07K 14/30* (2013.01); *C07K 16/00* (2013.01);
(Continued)

(58) Field of Classification Search
CPC ............. C07K 16/1253; G01N 33/558; G01N 33/56933; G01N 2333/30; G01N 2800/26
(Continued)

(56) References Cited

U.S. PATENT DOCUMENTS

| 4,666,851 A | 5/1987 | Lee |
| 5,641,638 A | 6/1997 | Bredt et al. |
| 2012/0244544 A1 | 9/2012 | Minagawa et al. |

FOREIGN PATENT DOCUMENTS

| CN | 104198703 | * 12/2014 | .......... G01N 33/532 |
| CN | 104198703 A | 12/2014 | |

(Continued)

OTHER PUBLICATIONS

Dallo et al., (Infection and Immun. Jul. 1996, vol. 64, No. 7; pp. 2595-2601). (Year: 1996).*

(Continued)

*Primary Examiner* — Jana A Hines
(74) *Attorney, Agent, or Firm* — Fitch, Even, Tabin & Flannery LLP

(57) ABSTRACT

The present invention aims at providing a specific antibody that can simply and rapidly detect *Mycoplasma pneumoniae* which is a causative bacterium of *mycoplasma* pneumonia, with high sensitivity, and also an immunological detection method and a kit containing the same antibody. The present invention makes it possible to diagnose infection with *Mycoplasma pneumoniae* more rapidly and specifically than the conventional method, by producing an antibody recognizing a specific epitope of P30 protein of *Mycoplasma pneumoniae* and performing an immunological detection using the antibody. Also, the present invention enables easy and rapid detection of *Mycoplasma pneumoniae* and diagnosis of infection with the same at a hospital or the like without need of specialized instruments or skilled techniques.

8 Claims, 1 Drawing Sheet

Specification includes a Sequence Listing.

(51) Int. Cl.
  *C07K 16/00* (2006.01)
  *C12N 15/02* (2006.01)
  *G01N 33/569* (2006.01)
  *C07K 14/30* (2006.01)
  *C12Q 1/04* (2006.01)
  *C12Q 1/6888* (2018.01)

(52) U.S. Cl.
  CPC ............ *C12N 15/02* (2013.01); *C12N 15/09* (2013.01); *C12Q 1/04* (2013.01); *C12Q 1/6888* (2013.01); *G01N 33/56933* (2013.01); *G01N 2333/30* (2013.01); *G01N 2469/00* (2013.01); *G01N 2469/10* (2013.01)

(58) Field of Classification Search
  USPC ........................................................ 435/7.32
  See application file for complete search history.

(56) References Cited

FOREIGN PATENT DOCUMENTS

| | | | |
|---|---|---|---|
| EP | 537497 A | 4/1993 | |
| JP | 63-084484 A | 4/1988 | |
| JP | S63-184064 A | 7/1988 | |
| JP | H05-304990 A | 11/1993 | |
| JP | 2013-072663 A | 4/2013 | |
| JP | 2016031353 * | 3/2016 | ....... G01N 33/56933 |
| WO | 2011/068189 A1 | 6/2011 | |
| WO | WO2015025968 * | 2/2015 | .............. C12P 21/08 |

OTHER PUBLICATIONS

International Search Report for PCT/JP2016/052382 dated Apr. 16, 2016 (4 pages).
Dallo SF, Lazzell AL, Chavoya A, Reddy SP, Baseman JB., Bio functional domains of the Mycoplasma pneumoniae P30 adhesin., Infect Immun., Jul. 1996, vol. 64, No. 7, p. 2595-2601.
Chang Hy, Jordan JL, Krause DC., Domain analysis of protein P30 in Mycoplasma pneumoniae cy tadherence and gliding motility., J Bacteriol., Apr. 2011, vol. 193, No. 7, p. 1726-1733.
International Preliminary Examination Report for PCT/JP2016/052382 dated Apr. 19, 2016 (5 pages).
Layh-Schmitt G, Himmelreich R, Leibfried U., The adhesin related 30-kDa protein of Mycoplasma pneumoniae exhibits size and antigen variability., FEMS Microbiol. Letters 152., Apr. 1997, p. 101-108.
CN Office Action, dated Aug. 27, 2018, in corresponding CN201680010102.9.
Written Opinion of the International Searching Authority (English Translation), issued in PCT/JP2016/052381 dated Apr. 19, 2016.
Supplementary European Search Report, dated Jun. 6, 2018, issued re EP Application 16 74 3434.
JPO decision dated Jun. 26, 2018 in JP appln 2016-572115.
Office Action in JP Appln. 2016-572114, dated Dec. 5, 2017.
Himmelreich et al., Complete sequence analysis of the genome of the bacterium Mycoplasma pneumoniae, Nucleic Acids Res., 24 (22):4420-49 (Nov. 15, 1996).
Office Action dated Jul. 18, 2019 re Japanese Patent Application No. 2016-572114.
SIPO (PRC) Office Action dated Jul. 2, 2019 re PRC Appln. 201680010102.9.
Third Office Action issued against corresponding Chinese Patent Application No. 201680010102.9 dated May 22, 2020; English translation submitted herewith (9 pages).
EPO Office Action apparently dated Jan. 31, 2019 that issued re EP Appln. 16 743 434.9.
Office Action issued against corresponding Japanese Patent Application No. 2018-178594 dated Aug. 19, 2020 English translation submitted herewith (8 pages).
Office Action dated Nov. 21, 2021 against corresponding KR Patent Application No. 10-2017-7022222; English translation submitted herewith (7 pages).
Mechetner, Development and Characterization of Mouse Hybridomas, Methods in Molecular Biology vol. 378 Monoclonal Antibodies: Methods and Protocols, edited by: M. Albitar, pp. 1-13, (Feb. 2007).
Paul, Fundamental Immunology, 2nd. Ed., Chapter 12, pp. 347-353 (1989).

* cited by examiner

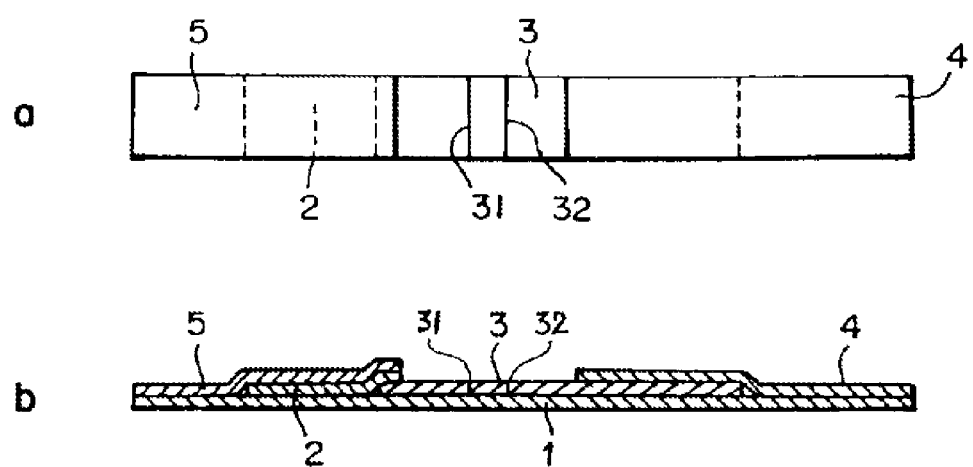

SEQUENCE LISTING

<160> NUMBER OF SEQ ID NOS: 7

<210> SEQ ID NO 1
<211> LENGTH: 274
<212> TYPE: PRT

<213> ORGANISM: Mycoplasma pneumoniae

<400> SEQUENCE: 1

Met Lys Leu Pro Pro Arg Arg Lys Leu Lys Leu Phe Leu Leu Ala Trp
1               5                   10                  15

Met Leu Val Leu Phe Ser Ala Leu Ile Val Leu Ala Thr Leu Ile Leu
            20                  25                  30

Val Gln His Asn Asn Thr Glu Leu Thr Glu Val Lys Ser Glu Leu Ser
        35                  40                  45

Pro Leu Asn Val Val Leu His Ala Glu Glu Asp Thr Val Gln Ile Gln
    50                  55                  60

Gly Lys Pro Ile Thr Glu Gln Ala Trp Phe Ile Pro Thr Val Ala Gly
65                  70                  75                  80

Cys Phe Gly Phe Ser Ala Leu Ala Ile Ile Leu Gly Leu Ala Ile Gly
                85                  90                  95

Leu Pro Ile Val Lys Arg Lys Glu Lys Arg Leu Ser Glu Glu Lys Glu
            100                 105                 110

Arg Gln Glu Gln Leu Ala Glu Gln Leu Gln Arg Ile Ser Ala Gln Gln
        115                 120                 125

Glu Glu Gln Gln Ala Leu Glu Gln Gln Ala Ala Ala Glu Ala His Ala
    130                 135                 140

Glu Ala Glu Val Glu Pro Ala Pro Gln Pro Val Pro Val Pro Pro Gln
145                 150                 155                 160

Pro Gln Val Gln Ile Asn Phe Gly Pro Arg Thr Gly Phe Pro Pro Gln
                165                 170                 175

Pro Gly Met Ala Pro Arg Pro Gly Met Pro Pro His Pro Gly Met Ala
            180                 185                 190

Pro Arg Ser Gly Phe Pro Pro Gln Pro Gly Met Ala Pro Arg Pro Gly
        195                 200                 205

Met Pro Pro His Pro Gly Met Ala Pro Arg Pro Gly Phe Pro Pro Gln
    210                 215                 220

Pro Gly Met Ala Pro Arg Pro Gly Met Pro Pro His Pro Gly Met Ala
225                 230                 235                 240

Pro Arg Pro Gly Phe Pro Pro Gln Pro Gly Met Ala Pro Arg Pro Gly
                245                 250                 255

Met Gln Pro Pro Arg Pro Gly Met Pro Pro Gln Pro Gly Phe Pro Pro
            260                 265                 270

Lys Arg

<210> SEQ ID NO 2
<211> LENGTH: 201
<212> TYPE: PRT
<213> ORGANISM: Mycoplasma pneumoniae

<400> SEQUENCE: 2

Phe Ile Pro Thr Val Ala Val Cys Phe Gly Phe Ser Ala Leu Ala Ile
1               5                   10                  15

Ile Leu Gly Leu Ala Ile Gly Leu Pro Ile Val Lys Arg Lys Glu Lys
            20                  25                  30

Arg Leu Leu Glu Glu Lys Glu Arg Gln Glu Gln Leu Ala Glu Gln Leu
        35                  40                  45

Gln Arg Ile Ser Ala Gln Gln Glu Gln Gln Ala Leu Glu Gln Gln
    50                  55                  60

Ala Ala Ala Glu Ala His Ala Glu Ala Glu Val Glu Pro Ala Pro Gln
65                  70                  75                  80

```
Pro Val Pro Val Pro Gln Pro Gln Val Gln Ile Asn Phe Gly Pro
             85                  90                  95

Arg Thr Gly Phe Pro Pro Gln Pro Gly Met Ala Pro Arg Pro Gly Met
            100                 105                 110

Pro Pro His Pro Gly Met Ala Pro Arg Pro Gly Phe Pro Pro Gln Pro
            115                 120                 125

Gly Met Ala Pro Arg Pro Gly Met Pro Pro His Pro Gly Met Ala Pro
        130                 135                 140

Arg Pro Gly Phe Pro Pro Gln Pro Gly Met Ala Pro Arg Pro Gly Met
145                 150                 155                 160

Pro Pro His Pro Gly Met Ala Pro Arg Pro Gly Phe Pro Pro Gln Pro
                165                 170                 175

Gly Met Ala Pro Arg Pro Gly Met Gln Pro Pro Arg Pro Gly Met Pro
            180                 185                 190

Pro Gln Pro Gly Phe Pro Pro Lys Arg
        195                 200
```

```
<210> SEQ ID NO 3
<211> LENGTH: 12
<212> TYPE: PRT
<213> ORGANISM: Mycoplasma pneumoniae

<400> SEQUENCE: 3

Gly Met Ala Pro Arg Pro Gly Met Pro Pro His Pro
1               5                   10

<210> SEQ ID NO 4
<211> LENGTH: 12
<212> TYPE: PRT
<213> ORGANISM: Mycoplasma pneumoniae

<400> SEQUENCE: 4

Gly Met Ala Pro Arg Pro Gly Phe Pro Pro Gln Pro
1               5                   10

<210> SEQ ID NO 5
<211> LENGTH: 13
<212> TYPE: PRT
<213> ORGANISM: Mycoplasma pneumoniae

<400> SEQUENCE: 5

Gly Met Ala Pro Arg Pro Gly Met Gln Pro Pro Arg Pro
1               5                   10

<210> SEQ ID NO 6
<211> LENGTH: 25
<212> TYPE: PRT
<213> ORGANISM: Mycoplasma pneumoniae

<400> SEQUENCE: 6

Lys Arg Lys Glu Lys Arg Leu Leu Glu Glu Lys Glu Arg Gln Glu Gln
1               5                   10                  15

Leu Ala Glu Gln Leu Gln Arg Ile Ser
            20                  25

<210> SEQ ID NO 7
<211> LENGTH: 20
<212> TYPE: PRT
<213> ORGANISM: Mycoplasma pneumoniae

<400> SEQUENCE: 7
```

-continued

```
Ala Gln Gln Glu Glu Gln Gln Ala Leu Glu Gln Gln Ala Ala Ala Glu
1               5                   10                  15
Ala His Ala Glu
            20
```

IMMUNOLOGICAL DETECTION METHOD AND KIT FOR *MYCOPLASMA PNEUMONIAE*

CROSS-REFERENCE TO RELATED APPLICATIONS

This application is a U.S. national phase application filed under 35 U.S.C. § 371 of International Application No. PCT/JP2016/052381, filed Jan. 27, 2016, designating the United States, which claims priority from Japanese Patent Application No. 2015-015253, filed Jan. 29, 2015, and the complete disclosures of such applications, including sequence listing(s), are hereby incorporated herein by reference in their entirety for all purposes.

SEQUENCE LISTING

The instant application contains a Sequence Listing which has been filed electronically in ASCII format and is hereby incorporated by reference in its entirety. Said ASCII copy, created on Jul. 28, 2017, is named 7378-141424-US_SL.txt and is 5,576 bytes in size.

TECHNICAL FIELD

The present invention relates to an antibody against P30 protein of *Mycoplasma pneumoniae*, and an immunological method and a kit for detecting *Mycoplasma pneumoniae* using the antibody.

BACKGROUND ART

*Mycoplasma* pneumonia is atypical pneumonia caused by *Mycoplasma pneumoniae*. *Mycoplasma* pneumonia, together with chlamydia pneumonia, constitutes 30% to 40% of the atypical pneumonia cases and also constitutes a high percentage of the community-acquired pneumonia cases.

*Mycoplasma* pneumonia is common in infants, children, and adolescence. The incubation period is 2 to 3 weeks. Excretion of the pathogen into respiratory mucosa is observed in 2 to 8 days before the onset of initial symptom, becomes the highest at the onset of clinical symptoms, continues at a high level for about one week, and then further continues for 4 to 6 weeks or more. Main clinical symptoms are fever, general malaise, headache, and other cold-like symptoms. *Mycoplasma* pneumonia is characterized by, for example, high fever greater than 38° C. and intense dry cough. The cough further continues for a long time, 3 to 4 weeks, after decline of fever. However, there is no examination finding characteristic to *mycoplasma* pneumonia, and pale ground-glass appearance in chest X-ray examination is typical.

The manner of infection with *Mycoplasma* is droplet infection and contact infection from an infected patient. *Mycoplasma pneumoniae* invades the respiratory tract and attaches to the bronchi or, bronchiole epithelium to achieve the infection.

*Mycoplasma* infection is designated as a notifiable infectious disease (Infectious diseases Category V) based on the Infectious Diseases Control Law, and designated medical care providers have an obligation to promptly report the number of patients.

*Mycoplasma pneumoniae* is a minimum microorganism that can replicate itself, and differs from other bacteria in that it does not have a cell wall.

Accordingly, β-lactam antibiotics and cephem antibiotics, which are antibiotics having a function of inhibiting cell wall synthesis, are ineffective, and macrolide antibiotics, tetracycline antibiotics and new quinolone antibiotics are administered for treatment. Prompt identification of the causative bacteria is therefore desired for determining a treatment plan.

At present, *Mycoplasma pneumoniae* infection is definitely diagnosed by an isolation culture method and a serological test.

The isolation culture needs a specialized culture medium (PPLO medium) for detecting *Mycoplasma*. In addition, its proliferation is slow, compared to other bacteria, thereby taking at least about one week for obtaining the result of determination. It is therefore difficult to rapidly identify the causative bacteria by the isolation culture method in clinical sites.

*Mycoplasma* is susceptible to temperature, and samples containing *Mycoplasma* cannot be kept in cold storage, unlike samples containing common bacteria. Accordingly, *Mycoplasma* contained in a sample may become extinct or decrease during storage or transportation of the sample and may not be detected even by the isolation culture method.

Examples of the serological test include a cold agglutination, a Complement Fixation (CF) test, an indirect hemagglutination (IHA) test, a particle agglutination (PA) method, and an enzyme immunoassay (EIA), which specifically detect IgG antibody or IgM antibody.

Furthermore, an immunochromatographic kit (Immuno-Card *Mycoplasma* Antibody, available from TFB, Inc.) is commercially available as a simple test detecting *Mycoplasma pneumoniae*-specific IgM antibody in serum or plasma by EIA and is used at clinical sites.

In the serological test, although the IgM antibody in a sample to be detected increases at the early stage of infection, the sample may show false negative in the case of low antibody production response or depending on assay timing. Furthermore, since it takes a long time before IgM antibody disappears in blood, it cannot be said that the result of the serological test always correctly indicates the current infection status.

Accordingly, definite diagnosis by the serological test needs quantitative tests using paired sera of acute and convalescent stages, and therefore has to be ex-post diagnosis in many cases.

A nucleic acid detection method for detecting DNA of *Mycoplasma pneumoniae* is also employed. In the nucleic acid detection method, however, the procedure of amplifying nucleic acid is complicated and needs specialized equipment, and the assay takes several hours. Thus, the method is not a test that is generally used.

In order to more rapidly and simply detect *Mycoplasma pneumoniae* infection, a specific antibody against *Mycoplasma pneumoniae* antigen has been developed, and a detection method of distinguishing whether *mycoplasma* infection is present or not has been reported.

*Mycoplasma pneumoniae* attaches itself to the respiratory epithelial cell cilia with its adhesive organ in a form of a flask-shaped protrusion, and then moves to the cell surface by gliding motility and adheres thereto to achieve the infection. Production of an antibody specific to P1 protein (169 KDa), which is known as adhesive protein playing a central role in this adhesion or gliding motility, and a detection method using the P1 protein as a detection marker have been reported (Patent Documents 1 and 2).

It is also known that P1 protein, the antigen to be detected reported in the above reports, has two genotypes and that the amino acid sequences corresponding to the genotypes of P1 protein are different from each other. Accordingly, in order to broadly detect *Mycoplasma pneumoniae*, production of each antibody against P1 protein of each P1 genotype or an antibody recognizing a common site of P1 protein of the different genotypes is necessary. In addition, seasonal epidemic has been reported such that a genotype different from the epidemic genotype in the latest season is detected, that is, the genotype changes depending upon epidemic seasons. Therefore, it is necessary to find out the genotype at an early stage of the epidemic and use an antibody specific thereto.

A detection method using DnaK protein, which is known to be conserved among isolated strains of *Mycoplasma pneumoniae* compared with P1 protein, as a detection marker (Patent Document 3) has been also reported. DnaK protein is also possessed by *Mycoplasma genitalium* causing human urinary infectious diseases, and therefore also shows cross reactivity. Consequently, *Mycoplasma pneumoniae* cannot be specifically detected by using the above protein as a detection marker.

Also, there is a report of mutant strains related to P30 protein (30kDa) which is an adhesion protein of *Mycoplasma pneumoniae* (Non-Patent Document 1). In this report, SDS-PAGE detection method using a rabbit antisera against P30 protein has been reported. A polypeptide having N-terminal amino acid sequence (102-181) and a polypeptide having C-terminal amino acid sequence (139-275) of P30 protein are expressed as a fusion protein with modified murine dihydrofolate reductase (DHFR) to produce rabbit antisera against the fusion protein. In this report, only the rabbit antisera having reactivity with P30 protein is disclosed, but no antibody recognizing a specific epitope in P30 protein is disclosed. Furthermore, it is unknown whether the antiserum can be used for immunological detection in the present invention, and is unclear whether it has a high specificity and reactivity.

If *mycoplasma* pneumonia is not appropriately treated, the symptoms may be protracted or become severe or may further cause the spread of the infection due to secondary infection. Accordingly, in order to select appropriate treatment and antibiotics, rapid and conclusive detection of *Mycoplasma pneumoniae* is demanded.

Furthermore, even though rapid detection of *Mycoplasma pneumoniae* has been contemplated, an antibody that can further specifically detect *Mycoplasma pneumoniae*, and also an immunoassay and a kit containing such an antibody have been demanded.

CONVENTIONAL TECHNICAL DOCUMENTS

Patent Documents

Patent Document 1: Japanese Patent Laid-Open No. H5-304990
Patent Document 2: Japanese Patent Laid-Open No. 2013-72663
Patent Document 3: International Publication No. WO2011/068189
Non-Patent Documents
Non Patent Document 1: G. Layh-Schmitt et al., "The adhesin related 30-kDa protein of *Mycoplasma peumoniae* exhibits size and antigen variability.", FEMS Microbiology Letters, 152, 1997, p. 101-108.

SUMMARY OF INVENTION

Problem to be Solved by the Invention

The present invention aims at specifically detecting the P30 protein of *Mycoplasma pneumoniae* in biological samples, thereby enabling highly accurate diagnosis of infection with *Mycoplasma pneumoniae* than before.

Means for Solving the Problem

The present inventors have succeeded in obtaining an antibody against a specific epitope of the P30 protein by immunizing a mouse using the P30 protein of *Mycoplasma pneumoniae* as an immunogen, and have found out that *Mycoplasma pneumoniae* can be detected more specifically with higher sensitivity than before by using the antibody in an immunoassay, especially a sandwich immunoassay, and particularly an immunochromatographic assay. Thus the present invention has been completed.

That is, according to one aspect of the present invention, there is provided a method of detecting *Mycoplasma pneumoniae*, comprising an immunoassay using an antibody against P30 protein of *Mycoplasma pneumoniae*, the antibody being an antibody against an epitope located in any one of amino acid sequences of SEQ ID NOS: 3 to 5.

Similarly, there is provided an immunoassay kit for *Mycoplasma pneumoniae*, comprising at least an antibody against P30 protein of *Mycoplasma pneumoniae*, the antibody being an antibody against an epitope of the P30 protein located in any one of amino acid sequences of SEQ ID NOS: 3 to 5.

In particular, the immunoassay in the above detection method and immunoassay kit is preferably a sandwich immunoassay such as an enzyme-linked immunosorbent assay (ELISA) and an immunochromatographic assay.

Therefore, according to another aspect of the present invention, there is provided a method of detecting *Mycoplasma pneumoniae*, comprising a sandwich immunoassay using first and second antibodies against P30 protein of *Mycoplasma pneumoniae*, wherein at least one of the first and second antibodies is an antibody against an epitope located in any one of amino acid sequences of SEQ ID NOS 3 to 5.

Similarly, there is provided a sandwich immunoassay kit for *Mycoplasma pneumoniae*, comprising at least first and second antibodies against P30 protein of *Mycoplasma pneumoniae*, wherein at least one of the first and second antibodies is an antibody against an epitope of the P30 protein located in any one of amino acid sequences of SEQ ID NOS: 3 to 5.

According to a preferred embodiment of the present invention, there is provided an immunochromatographic assay for detecting *Mycoplasma pneumoniae*, comprising:

providing a membrane carrier having a capturing zone which is formed by previously immobilizing a first antibody against P30 protein of *Mycoplasma pneumoniae* at a predetermined position;

chromatographically developing a liquid mixture in the membrane carrier toward the capturing zone, said liquid mixture containing a second antibody against the P30 protein and a predetermined amount of a test sample, whereby a complex of an antigen contained in the test sample and the second antibody is captured by the capturing zone, wherein at least one of the first and second antibodies is an antibody against an epitope located in any one of amino acid sequences of SEQ ID NOS: 3 to 5.

According to another preferred embodiment of the present invention, there is provided a *Mycoplasma pneumoniae*-detecting immunochromatographic test strip, comprising at least first and second antibodies against P30 protein of *Mycoplasma pneumoniae* and a membrane carrier, wherein the first antibody is previously immobilized at a predetermined position of the membrane carrier so as to form a capturing zone; and the second antibody is labeled with an appropriate labeling substance and is provided at a position separated from the capturing zone so as to be chromatographically developed in the membrane carrier, wherein at least one of the first and second antibodies is an antibody against an epitope located in any one of amino acid sequences of SEQ ID NOS: 3 to 5.

Although the antibody against the P30 protein, which is essentially used in the present invention and is an antibody against an epitope located in any one of amino acid sequences of SEQ ID NOS: 3 to 5, may be a polyclonal antibody or a monoclonal antibody, preferred is a monoclonal antibody from the viewpoint of reaction specificity.

The amino acid sequences of SEQ ID NOS: 3 to 5 constitute parts of the entire amino acid sequence of the P30 protein set forth in SEQ ID NO: 1 and are regions containing an epitope of the P30 protein.

In a sandwich immunoassay such as immunochromatographic assay, although the first and second antibodies used therein may be each a polyclonal antibody or a monoclonal antibody, from the viewpoint of reaction specificity, generally speaking, at least one of the antibodies is preferably a monoclonal antibody, and both antibodies are particularly preferably monoclonal antibodies. In addition, a large number of P30 protein molecules are present and are localized on the cell surface. In order to avoid competition between antibodies used therein and to obtain higher reactivity, the first antibody and the second antibody are preferably antibodies against different epitopes of P30 protein.

Incidentally, the P30 protein of *Mycoplasma pneumoniae* to which the antibody for detecting *Mycoplasma pneumoniae* according to the present invention reacts is a protein necessary for adhesion of *Mycoplasma* to a host cell and is known as one of the accessory proteins that work together with an adhesion factor P1 protein.

The P30 protein has a molecular weight of 30 KDa and is one of the adhesive proteins involved in adhesion and pathogenicity, like P1 protein. In the *Mycoplasma pneumoniae* cell, the P30 protein is localized on the cell surface at an end of the adhesive organ and is a transmembrane protein having the N-terminal region embedded in the cell membrane and the C-terminal region present outside the cell membrane. The P30 protein includes an amino acid sequence containing a large number of proline on the C-terminal region and has a repeating structure of such a sequence. In general, a region having an amino acid sequence containing a large number of proline is known to form a three-dimensional conformation and is known to have a high possibility of becoming an epitope reactive with an antibody.

The antibody used in the present invention is an antibody against an epitope located in any one of amino acid sequences of SEQ ID NOS: 3 to 5 that are contained in the whole amino acid sequence of the P30 protein shown in SEQ ID NO: 1. Also, such antibodies react with *Mycoplasma pneumoniae* only, but do not react with any other *Mycoplasma* bacteria, and thus are excellent in specificity. The amino acid sequences of SEQ ID NOS: 3 to 5 are each a region including an epitope of P30 protein. Therefore, the antibodies used in the present invention can be each paraphrased as an antibody which can cause antigen-antibody reaction with a fragment of P30 protein having 12 to 15 amino acid residues contained in any one of amino acid sequences of SEQ ID NOS: 3 to 5.

Thus, according to another aspect of the present invention, there is provided an antibody recognizing an epitope of P30 protein located in any one of amino acid sequences of SEQ ID NOS: 3 to 5.

Effect of Invention

According to the present invention, infection with *Mycoplasma pneumoniae* can be rapidly and specifically diagnosed by producing an antibody specifically reactive to *Mycoplasma pneumoniae* P30 protein and performing an immunological assay using the P30 protein as a detection marker. The immunological assay and assay apparatus of the present invention enables the diagnosis of infection with *Mycoplasma pneumoniae* to be made more simply and rapidly than before, at a hospital or another facility without need of any specialized equipment or skill.

According to the present invention, an antibody against an epitope located in any one of the amino acid sequences of SEQ ID NOS: 3 to 5 contained in the whole amino acid sequence of P30 protein shown in SEQ ID NO: 1 is used in the immunoassay-based detection method, and thus the diagnosis of infection with *Mycoplasma pneumoniae* can be performed with higher accuracy than before, and the detection can be made with higher sensitivity at an earlier stage.

BRIEF DESCRIPTION OF DRAWING

FIG. 1a is a plan view of an immunochromatographic test strip, and FIG. 1b is a vertical cross-sectional view of the immunochromatographic test strip shown in FIG. 1a.

DESCRIPTION OF EMBODIMENTS

In the present invention, each step in production of an antibody and detection or assay method using the antibody is performed in conformity with each immunological procedure known per se.

In the present invention, a polyclonal antibody can be obtained, for example, by cloning a DNA fragment corresponding to an amino acid sequence of SEQ ID NOS: 3 to 5 from the DNA sequence encoding the amino acid sequence shown in SEQ ID NO: 1, allowing the cloned gene to express in a host such as *Escherichia coli* in a genetic engineering manner, extracting and purifying the expressed protein, and immunizing an animal with the purified protein being used as an antigen according to an ordinary method, and then obtaining the polyclonal antibody from the antiserum of the immunized animal.

In the present invention, a monoclonal antibody can be obtained, for example, by immunizing an animal such as a mouse with the above purified protein being used as an antigen, fusing the splenic cells of the immunized animal with myeloma cells for cell fusion, selecting the thus fused cells in a HAT-containing medium and allowing them to grow, and then selecting the grown strains using the above polypeptide of an amino acid sequence of SEQ NOS: 3 to 5 by an enzyme-labeled immunoassay or the like.

Alternatively, the monoclonal antibody can be obtained, for example, by purifying P30 protein from *Mycoplasma pneumoniae*, immunizing an animal such as a mouse with the P30 protein being used as an antigen, fusing the splenic cells of the immunized animal with myeloma cells for cell fusion, selecting the thus fused cells in a HAT-containing medium and allowing them to grow, and then selecting a strain reactive with a polypeptide of SEQ ID NOS: 3 to 5 from the grown strains.

Examples of the antibody of the present invention include not only antibodies but also antibody fragments and modified antibodies substantially equivalent to the antibodies as having a reactivity with a polypeptide of an amino acid sequence of SEQ ID NOS: 3 to 5 contained in the P30 protein of *Mycoplasma pneumoniae*. Examples of the antibody fragments include Fab fragments, F(ab')$_2$ fragments, Fab' fragments, and scFv fragments.

The immunochromatographic assay of the present invention for detecting *Mycoplasma pneumoniae* in a test sample can be practiced easily in accordance with the structure of a known immunochromatographic test strip.

Generally, such an immunochromatographic test strip is constituted by at least a first antibody which is capable of undergoing antigen-antibody reaction at a first antigenic determinant of an antigen, a second antibody which is labeled and capable of undergoing antigen-antibody reaction at a second antigenic determinant of the antigen, and a membrane carrier, wherein the first antibody is previously immobilized in a predetermined position of the membrane carrier so as to form a capturing zone, and the second antibody is placed at a position separated from the capturing zone so as to be allowed to be chromatographically developed in the membrane carrier. Although the first antibody and the second antibody may be each a polyclonal antibody or a monoclonal antibody as described above, at least one of them is preferably a monoclonal antibody. The first antibody and the second antibody are generally used in a "hetero" combination. That is, the first and second antibodies which recognize the respective antigenic determinants different in both position and conformation on an antigen are used in combination. However, the first antigenic determinant and the second antigenic determinant may have the same conformation as long as they are different in position on the antigen, and in such a case, the first antibody and the second antibody may be monoclonal antibodies in a "homo" combination, that is, one and the same monoclonal antibody can be used as both the first antibody and the second antibody.

As a specific example, mention may be made of a test strip as shown in FIG. 1. In FIG. 1, the numeral 1 indicates an adhesive sheet, 2 indicates an impregnated member, 3 indicates a membrane carrier, 31 indicates a capturing zone, 32 indicates a control capturing zone, 4 indicates an absorbing member, and 5 indicates a sample-receiving member.

In the example shown in the drawing, the membrane carrier 3 consists of an elongated strip-shaped nitrocellulose membrane filter having a width of 5 mm and a length of 36 mm.

In the membrane carrier 3, a first antibody is immobilized at a position of 7.5 mm from the end on the starting side of chromatographic development, so as to form a capturing zone 31 of an analyte. Furthermore, the membrane carrier 3 is provided with a control capturing zone 32 at a position of 15 mm from the end on the starting side of chromatographic development. This control capturing zone 32 is provided for verifying whether the reaction is performed or not regardless of the presence or absence of an analyte and can be usually formed by immobilizing a material (excluding the analyte) specifically immunologically binding to the second antibody to the membrane carrier 3. For example, when an antibody derived from a mouse is used as the second antibody, an antibody against the mouse antibody can be used.

In the example shown in the figure, a nitrocellulose membrane filter is used as the membrane carrier 3. However, any type of membrane carrier can be used herein, as long as it is able to chromatographically develop an analyte contained in a test sample and immobilize an antibody that forms the capturing zone 31. Thus, other types of cellulose membranes, nylon membranes, glass fiber membranes, or the like can also be used.

The impregnation member 2 comprises a member impregnated with a second antibody that undergoes antigen-antibody reaction with the antigen at a second antigenic determinant located at a site different from the first antigenic determinant to which the first antibody binds. The second antibody is previously labeled with an appropriate labeling substance.

In the example as shown in the figure, a strip-shaped glass fiber nonwoven fabric having a size of 5 mm×15 mm is used as the impregnated member 2. However, the impregnated member 2 is not limited thereto, but includes, for example, cellulose fabrics (a filter paper, a nitrocellulose membrane, etc.), porous plastic fabrics such as of polyethylene and polypropylene, and others.

As a labeling substance that labels the second antibody, any substance can be used, as long as it is usable herein. Examples of such a labeling substance include a color labeling substance, an enzyme labeling substance, a fluorescent labeling substance, and a radiation labeling substance. Of these, a color labeling substance is preferably used because observation of a color change in the capturing zone 31 with naked eyes enables rapid and simple determination.

Examples of the color labeling substance include colloidal metals, such as colloidal gold and colloidal platinum; and latexes, such as synthetic latexes such as polystyrene latexes colored with pigments such as red and blue pigments and natural rubber latexes. Among these, colloidal metals, such as colloidal gold, are particularly preferred.

The impregnation member 2 can be produced, for example, by impregnating a member, such as the above-mentioned glass fiber non-woven fabric, with a suspension of a labeled second antibody and drying it.

As shown in FIG. 1, the immunochromatographic test strip of the present invention can be produced as follows. The membrane carrier 3 is affixed to the middle of the adhesive sheet 1. On the end on the starting side of chromatographic development (that is, the left side in FIG. 1 which is hereinafter referred to as an "upstream side" whilst the opposite side, that is, the right side in FIG. 1 is hereinafter referred to as a "downstream side") of the membrane carrier 3, the downstream side end of the impregnated member 2 is laid so as to communicate them. The upstream side zone of the impregnated member 2 is affixed to the adhesive sheet 1.

Moreover, if necessary, the downstream side zone of a sample-receiving member 5 may be placed on the upper face of the impregnated member 2 whilst the upstream side zone of the sample-receiving member 5 may also be affixed to the adhesive sheet 1. Furthermore, the upstream side zone of an absorbing member 4 may be placed on the upper face of the downstream side zone of the membrane carrier 3 whilst the downstream side zone of the absorbing member 4 may be affixed to the adhesive sheet 1.

The absorbing member 4 may be made of any material as long as it is able to quickly absorb and retain a liquid. Examples of such a material include cotton fabrics, filter paper, and porous plastic nonwoven fabrics made from polyethylene, polypropylene, etc. In particular, filter paper is optimal. Also, a filter paper made of a composite material containing a water absorptive polymer may be used.

As the sample-receiving member 5, may be used, for example, a sheet or film of a porous synthetic resin such as porous polyethylene and porous polypropylene, or cellulose paper or a woven or nonwoven fabric such as a filter paper and a cotton fabric.

Furthermore, the immunochromatographic test strip shown in FIG. 1 can be provided in a state of being accommodated in an appropriate plastic case having a test sample injection portion and a determination portion which are respectively opened above the sample-receiving member 5 and the capturing zone 31. In order to prevent secondary infection of a user, the immunochromatographic test strip is preferably provided in a state being accommodated in the plastic case.

Then, a test sample constituted by a biological sample or the like is, if required, mixed with a suitable developing solvent so as to obtain a liquid mixture that can be developed chromatographically. Thereafter, the liquid mixture is injected into the sample-receiving member 5 of the immunochromatographic test strip as shown in FIG. 1, so that it passes through the sample-receiving member 5 and is mixed with a labeled second antibody at the impregnated member 2.

In this instance, if an analyte exists in the aforementioned liquid mixture, a complex of the analyte and the second antibody is formed as a result of antigen-antibody reaction. This complex is developed chromatographically in the membrane carrier 3, and then reaches the capturing zone 31 and is captured by the first antibody immobilized therein as a result of antigen-antibody reaction.

In this instance, if a color labeling substance such as colloidal gold is used as a labeling substance, the analyte can be immediately determined qualitatively or quantitatively based on coloring caused by accumulation of the color labeling substance at the capturing zone 31. Furthermore, the intensity of the coloring can be digitized and can be quantitatively measured by optically reading the intensity of the coloring of the color labeling substance accumulated on the capturing zone 31 of the immunochromatographic test strip with an immunochromatography reader.

In addition, when the chromatographic development is normally performed, the second antibody not involved in the antigen-antibody reaction with the analyte reaches the control capturing zone 32 and is captured by an antibody that is immobilized therein and reactive to the second antibody. On this occasion, if a color labeling substance is used as a labeling substance, the control capturing zone 32 colors by accumulation of the color labeling substance to confirm that the chromatographic development has been normally performed. In contrast, if the control capturing zone 32 does not color, it indicates that a problem such as no development of the second antibody happens.

Any test sample can be used. For example, it may be a biological sample in which *Mycoplasma pneumoniae* may be present, such as nasal cavity aspirate, nasopharynx aspirate, nasal cavity swab, throat swab, nasopharynx swab, sputum, saliva, and bronchial washings. The test sample may be diluted with an appropriate diluent such as physiological saline and developing solvent before it is applied to the membrane carrier.

When a test sample contaminated with blood is used in a test, in particular, using an antibody labeled with a color labeling substance such as colloidal gold, a hematocyte-capturing membrane member is preferably disposed on the sample receiving member. The hematocyte-capturing membrane member is preferably laminated between the aforementioned impregnated member and the aforementioned sample-receiving member. This inhibits development of erythrocytes in the membrane carrier and thus facilitates the confirmation of accumulation of color labeling substances in the capturing zone of the membrane carrier. As such a hematocyte-capturing membrane member, a carboxymethyl cellulose membrane is used. Specifically, an ion exchange filter paper CM (trade name) available from Advantec Toyo K.K., an ion exchange cellulose paper available from Whatman Japan K.K., etc. can be used.

EXAMPLES

The present invention will be described more specifically by way of the following examples, but is not limited to the examples.

Example 1

Expression and Purification of Recombinant P30 Protein

The amino acid sequence of P30 protein of *Mycoplasma pneumoniae* M129 strain was obtained from a database of DNA Data Bank of Japan (DDBJ). An extracellular region excluding a transmembrane domain, the amino acid sequence (AA74-274) set forth in SEQ ID NO: 2, was specified from the amino acid sequence of the P30 protein, and a gene sequence corresponding to the amino acid sequence was synthesized. A His-tag expression vector, pET302/NT-His, was cleaved with a restriction enzyme, EcoRI, was then dephosphorylated using an alkaline phosphatase, and was mixed with the gene sequence, followed by a ligation reaction using DNA Ligation Kit Ver. 2 (Takara Bio Inc.). The recombinant P30 plasmid carrying the target gene was introduced into a recombinant protein-expressing host, *E. coli* BL (DE3) pLysS (Novagen). The host bacteria were cultured on an LB agar plate medium. The resulting colonies were cultured in an LB liquid medium. Subsequently, 1 mM IPTG (Takara Bio Inc.) was added to the medium to induce expression of recombinant P30 protein, and *E. coli* was then collected. The collected bacteria were resuspended in a solubilization buffer (0.5% Triron X-100 (Sigma), 10 mM imidazole, 20 mM phosphate, and 0.5 M NaCl (pH 7.4) (Amersham)) and were solubilized by ultrasonication. The recombinant P30 protein was then purified with His trap Kit (Amersham). This purified protein was dialyzed against a phosphate buffered saline (hereinafter, referred to as PBS) to obtain a target recombinant P30 protein.

Example 2

Production of Monoclonal Antibody Against Recombinant P30 Protein

The recombinant P30 protein prepared in Example 1 was used as an antigen for immunization to produce a monoclonal antibody against the recombinant P30 protein (hereinafter, referred to as anti-P30 antibody). The monoclonal antibody was produced in accordance with an ordinary method. The recombinant P30 protein (100 μg) was mixed with an equal amount of Complete Freund's Adjuvant (Difco). A mouse (BALB/c, 5 weeks old, Japan SLC, Inc.) was immunized with the mixture three times, and the spleen cells of the mouse were used in cell fusion using Sp2/0-Ag14 mouse myeloma cells (Shulman, et al., 1978). The cells were cultured in a culture solution prepared by adding L-glutamine (0.3 mg/mL), penicillin G potassium (100 unit/mL), streptomycin sulfate (100 μg/mL), and Gentacin (40 μg/mL) to Dulbecco's Modified Eagle Medium (DMEM) (Gibco) and also adding fetal calf serum (JRH) thereto in an amount of 10%. The cell fusion was performed by mixing immunized mouse spleen cells with Sp2/0-Ag14 cells and adding polyethylene glycol solution (Sigma) to the mixture. The hybridomas were cultured in HAT-DMEM (serum-added DMEM containing 0.1 mM sodium hypoxanthine, 0.4 μM aminopterin, and 0.016 mM thymidine (Gibco)). Antibody production in the culture supernatant was verified by enzyme-linked immunosorbent assay (ELISA). Antibody production-positive cells were cultured in HT-DMEM (serum-added DMEM containing 0.1 mM sodium hypoxanthine and 0.16 mM thymidine) and were further continuously cultured in serum-added DMEM.

Example 3

Preparation of Monoclonal Antibody

A mouse (BALB/c, retired, Japan SLC, Inc.), inoculated with 2,6,10,14-tetramethylpentadecane (Sigma) in advance, was intraperitoneally inoculated with the cloned cells, and the ascites was collected. The ascites was applied to a protein G column to purify a monoclonal antibody. The isotype of the produced monoclonal antibody was identified by Mouse Monoclonal Antibody Isotyping Reagents (Sigma).

Eventually, six clones of cells producing monoclonal antibodies against P30 protein were obtained.

Reference Example 1

Production of Standard Bacterial Solution for Test

PPLO media were inoculated with standard strains of *Mycoplasma pneumoniae* M129 strain and FH strain, followed by culturing in an atmosphere of 5% $CO_2$ at 37° C. until the desired concentration was obtained. The resulting culture solution was 10-fold serially diluted with a PPLO liquid medium until giving 100000-fold diluted solution. The number of grown colonies in each diluted solution on the PPLO agar medium was counted under a stereomicroscope to calculate the bacterial concentration. The resulting culture solutions were used as bacterial solutions for tests.

Comparative Example 1

Purification of *Mycoplasma Pneumoniae* P1 Protein

A PPLO liquid medium was inoculated with a *Mycoplasma pneumoniae* M129 strain, followed by culturing at 37° C. The resulting culture solution was centrifuged to collect the cells. P1 protein was purified from the cells in accordance with the method of Nakane, et al. (Journal of Bacteriology, 2011).

The resulting cells were washed with a PBS, pH 7.4, twice. The cells were suspended in a PBS containing 1% CHAPS, and the suspension was centrifuged. The resulting sediment was then dissolved in a PBS containing 2% octylglucoside. The solution was centrifuged, and the supernatant was collected. The resulting supernatant was subjected to ammonium sulfate fractionation, followed by centrifugation. The resulting sediment was dissolved in a PBS containing 0.3% Triton X-100, and the solution was purified by gel filtration column chromatography using Superdex 200. The fraction containing the purified protein was analyzed by SDS-page to confirm a single band at about 170 kDa. Thus, target P1 protein was obtained.

Example 4

Epitope Analysis of Anti-P30 Antibody

Amino acid sequences that are present in proline-rich regions on N-terminal side and thus may form epitopes were selected from the amino acid sequence of P30 protein derived from *Mycoplasma pneumoniae* of SEQ ID NO: 1, and polypeptides having amino acid sequences of SEQ ID NOS: 3 to 5 were synthesized. The synthesized polypeptides had sequences of GMAPRPGMPPHP (SEQ ID NO: 3) of No. 178 to No. 189, GMAPRPGFPPQP (SEQ ID NO: 4) of No. 190 to No. 201 and GMAPRPGMQPPRP (SEQ ID NO: 5) of No. 250 to No. 262 from the N-terminal of the amino acid sequence of SEQ ID NO: 1. Meanwhile, the same sequence as the sequence shown in SEQ ID NO: 3 is present between No. 202 and No. 213 and between No. 226 to No. 237 from the N-terminal, and also the same sequence as the sequence shown in SEQ ID NO: 4 is present between No. 214 and No. 225 and between No. 238 and No. 249 from the N-terminal. That is, a plurality of amino acid sequences of SEQ ID NOS: 3 and 4 exist in P30 protein so as to provide repeating structures.

Peptides having amino acid sequences of SEQ ID NOS: 3 to 5 were added to a 96-well microplate and immobilized. As controls, *M. pneumoniae* purified cells, the purified P30 protein prepared in Example 1, polypeptides having sequences of KRKEKRLLEEKERQEQLORIS (SEQ ID NO: 6) of No. 101 to No. 125 and AQQE-EQQALEQQAAAEAHAE (SEQ ID NO: 7) of No. 126 to No. 145 from the N-terminal of P30 protein, and the P1 protein of *Mycoplasma pneumoniae* prepared in Reference Example 1 were immobilized, and the reactivity with the monoclonal antibodies produced in Example 3 was confirmed in the same manner as above.

Monoclonal antibodies produced in Example 3 were added to the microplate to which the peptides were immobilized at prescribed concentrations, followed by incubation at room temperature for 1 hour. Subsequently, the solution in each well was sucked and removed. After washing, a biotin-labeled anti-mouse antibody was added for reaction. After incubation for 1 hour, the solution in each well was sucked and removed. After washing, avidin-labeled horse radish peroxidase was added for reaction. A 3,3',5,5'-tetramethyl-benzidine (TMBZ) solution was then added as a chromogenic substrate for reaction. The reaction was stopped with 2N sulfuric acid. The absorbance was measured with a microplate reader (Biorad) at a main wavelength of 450 nm. The results are shown in Table 1.

TABLE 1

| | Immobilized antigen | | | | | | | |
| --- | --- | --- | --- | --- | --- | --- | --- | --- |
| | SEQ ID NO: 3 | SEQ ID NO: 4 | SEQ ID NO: 5 | P30 protein | SEQ ID NO: 6 | SEQ ID NO: 7 | P1 protein | M. pneumoniae purified cells |
| BLMP001 | 0.894 | 1.021 | 1.863 | 1.813 | 0.062 | 0.051 | 0.012 | 2.124 |
| BLMP002 | 2.301 | 0.541 | 0.721 | 1.851 | 0.051 | 0.026 | 0.025 | 2.052 |
| BLMP003 | 0.781 | 2.012 | 0.621 | 1.921 | 0.021 | 0.047 | 0.014 | 1.856 |
| BLMP004 | 1.729 | 1.531 | 1.621 | 2.120 | 0.042 | 0.031 | 0.037 | 1.741 |
| BLMP005 | 0.062 | 0.051 | 0.043 | 1.613 | 1.593 | 0.042 | 0.042 | 1.684 |
| BLMP006 | 0.021 | 0.044 | 0.025 | 1.489 | 0.027 | 1.626 | 0.018 | 1.729 |

From the above results, the monoclonal antibody BLMP001 showed the strongest reaction with the polypeptide having the amino acid sequence of SEQ ID NO: 5. Also, it showed a reaction with the polypeptides having similar sequences, namely, the polypeptide having the amino acid sequence of SEQ ID NO: 3 and the polypeptide having the amino acid sequence of SEQ ID NO: 4.

The monoclonal antibody BLMP002 showed a strong reaction with the polypeptide having the amino acid sequence of SEQ ID NO: 3, and the monoclonal antibody BLMP003 showed a strong reaction with the polypeptide having the amino acid sequence of SEQ ID NO: 4. They showed a reactivity with other polypeptides having the similar amino acid sequences, as the monoclonal antibody BLMP001 did.

The monoclonal antibody BLMP004 showed a reaction with all the polypeptides having the amino acid sequence of SEQ ID NO: 3, SEQ ID NO: 4 and SEQ ID NO: 5. It is assumed to be a monoclonal antibody recognizing a sequence common in the respective amino acid sequences.

The monoclonal antibodies BLMP001, BLMP002 and BLMP003 showed a strong reaction with the *Mycoplasma pneumoniae* purified cells and the purified P30 protein but showed no reaction with the purified P1 protein as a control.

Therefore, it was confirmed that the monoclonal antibody BLMP001 is an antibody recognizing a polypeptide having the amino acid sequence of SEQ ID NO: 5 in the P30 protein, the monoclonal antibody BLMP002 is an antibody recognizing a polypeptide having the amino acid sequence of SEQ ID NO: 3, and the monoclonal antibody BLMP003 is an antibody recognizing a polypeptide having the amino acid sequence of SEQ ID NO: 4.

Example 5

Production of Immunochromatographic Test Strip Using Anti-P30 Antibody (1) Preparation of Anti-P30 Antibody Mice were intraperitoneally inoculated with monoclonal antibody BLMP001 producing cells or monoclonal antibody BLMP004 producing cells prepared in Example 3, and the ascites obtained from each mouse was purified with protein G by an ordinary method to obtain IgG which was used as an anti-P30 antibody.

(2) Preparation of Platinum-Gold Colloidal Particle Solution

Glassware to be used was all washed with aqua regia. Ultrapure water (390 mL) was boiled in a flask, and an aqueous chloroauric acid solution (30 mL, 1 L of the aqueous solution contains 1 g of gold, manufactured by Katayama Chemical Industries Co., Ltd.) was added to the boiling water. A 1 wt % aqueous sodium citrate solution (60 mL) was then added to the flask, and after 6 min and 45 sec, an aqueous chloroplatinic acid solution (30 mL, 1 L of the aqueous solution contains 1 g of platinum, manufactured by Wako Pure Chemical Industries, Ltd.) was added thereto. At 5 min after the addition of the aqueous chloroplatinic acid solution, a 1 wt % aqueous sodium citrate solution (60 mL) was added thereto, followed by reflux for 4 hours to obtain a platinum-gold colloidal suspension.

(3) Preparation of Platinum-Gold Colloid-Labeled Anti-P30 Antibody Solution

The monoclonal antibody BLMP001 obtained in the above section (1) was used as an anti-P30 antibody to be labeled with the platinum-gold colloid, and the labeling with the platinum-gold colloid was performed by the following procedure.

The anti-P30 antibody (1 µg in terms of protein weight, hereinafter, the weight of an antibody in terms of protein weight is simply shown by a numerical value of weight obtained by gravimetric analysis of the purified protein) and the platinum-gold colloidal solution (1 mL) described in the above section (2) were mixed, and the mixture was left to stand at room temperature for 2 minutes to allow all of the antibody to bind to the surfaces of the platinum-gold colloidal particles. An aqueous 10% bovine serum albumin (hereinafter, referred to as "BSA") solution was then added thereto at a final concentration of 1% in the platinum-gold colloidal solution to block all of the residual surfaces of the platinum-gold colloidal particles with BSA. Thus, a platinum-gold colloid-labeled anti-P30 antibody (hereinafter, referred to as "platinum-gold colloid-labeled antibody") solution was prepared. This solution was centrifuged (5600× G, for 30 min) to precipitate the platinum-gold colloid-labeled antibody, and the supernatant was removed to obtain a platinum-gold colloid-labeled antibody. This platinum-gold colloid-labeled antibody was suspended in a 50 mM tris hydrochloric acid buffer solution (pH 7.4) containing 10% saccharose, 1% BSA, and 0.5% Triton-X 100 to obtain a platinum-gold colloid-labeled antibody solution.

(4) Production of Immunochromatographic Test Strip Detecting P30 Protein of *Mycoplasma pneumoniae*

(4-1) Capturing zone of complex of P30 protein of *Mycoplasma pneumoniae* and gold colloid-labeled antibody An elongated strip-shaped nitrocellulose membrane with a size of 5 mm width and 36 mm length was provided as a membrane carrier 3 for chromatographic development of a chromatographic medium. 0.5 µL of a solution containing 1.0 mg/ml anti-P30 antibody was applied in a linear form to a position of 7.5 mm from the end on the starting point side of the chromatographic development of the membrane carrier 3 for chromatographic development. It was dried at room temperature, to form a capturing zone 31 for capturing a complex of the P30 protein and the platinum-gold colloid-labeled antibody. The applied anti-P30 antibody was the monoclonal antibody BLMP004 obtained in the above section (1).

(4-2) platinum-gold colloid-labeled antibody-impregnated member

A strip-shaped glass fiber nonwoven fabric with a size of 5 mm×15 mm was impregnated with 37.5 µL of the platinum-gold colloid-labeled antibody solution, and then dried at room temperature, to obtain a platinum-gold colloid-labeled antibody impregnated member 2.

(4-3) Preparation of immunochromatographic test strip

In addition to the membrane carrier 3 for chromatographic development and the labeled antibody-impregnated member 2, a cotton fabric as the sample-receiving member 5 and a filter paper as the absorbing member 4 were prepared. Then, a chromatographic test strip which was the same as FIG. 1 was prepared using these members.

(5) Test

The cultured bacterial solutions of M129 strain and FH strain of *Mycoplasma pneumoniae* were diluted with a sample extraction solution into a prescribed concentration to prepare each test sample. The test sample (100 µL) was dropwise added with a micropipette to the sample receiving member 5 of the test strip described in the above section (4) for chromatographic development by being left to stand at room temperature for 15 minutes. The captured amount of the complex of the P30 protein and the platinum-gold colloid-labeled antibody captured by the capturing zone 31 was observed with the naked eye.

The captured amount was determined by evaluating the degree of blacking, which is proportional to the amount, with the naked eye and classified into the following five stages: − (no blacking), ± (slight blacking), + (clear blacking), ++ (noticeable blacking), and +++ (extremely noticeable blacking). The cultured bacterium solution of *M. genitalium* was used as a negative control at a predetermined concentration.

Table 2 shows the results. As obvious from Table 2, high reactivity was shown with the two strains of *Mycoplasma pneumoniae*, and negativity was shown in all the tested concentrations against *M. genitalium* as the negative control. It was revealed that *Mycoplasma pneumoniae* can be detected with high sensitivity and high accuracy by the immunochromatographic assay using the two types of anti-P30 antibody.

TABLE 2

|  |  | *M. pneumoniae* M129 strain | *M. pneumoniae* FH strain | *M. genitalium* |
|---|---|---|---|---|
| Concentration (CFU/ml) | Blank | − | − | − |
|  | 1 × 10$^4$ | ± | ± | − |
|  | 1 × 10$^5$ | + | ±~+ | − |
|  | 1 × 10$^6$ | ++ | + | − |
|  | 1 × 10$^7$ | +++ | ++ | − |

Example 6

Comparative Reactivity Test of P30 Protein-Detecting Immunochromatographic Test Strip and P1 Protein-Detecting Immunochromatographic Test Strip The cultured bacterial solutions of M129 strain and FH strain of *Mycoplasma pneumoniae* prepared in Reference Example 1 were diluted with a sample extraction solution into a prescribed concentration to prepare each test sample. The test sample (100 µL) was dropwise added with a micropipette to the sample receiving member 5 of each immunochromatographic test strip for chromatographic development by being left to stand at room temperature for 15 minutes. The complex of the antigen and the platinum-gold colloid-labeled antibody captured by the capturing zone 31 was observed with the naked eye to determine the result. The captured amount was determined by evaluating the degree of blacking, which is proportional to the amount, with the naked eye and classified into the following five stages: − (no blacking), ± (slight blacking), + (clear blacking), ++ (noticeable blacking), and +++ (extremely noticeable blacking). As the conventional method, a commercially available reagent for detecting P1 protein of *Mycoplasma pneumoniae* was used. The results are shown in Table 3.

TABLE 3

|  |  | *M. pneumoniae* M129 strain | | *M. pneumoniae* FH strain | | *M. genitalium* | |
|---|---|---|---|---|---|---|---|
|  |  | Present invention | Conventional method | Present invention | Conventional method | Present invention | Conventional method |
| Concentration (CFU/ml) | Blank | − | − | − | − | − | − |
|  | 1 × 10$^4$ | ± | − | ± | − | − | − |
|  | 1 × 10$^5$ | ±~+ | − | + | − | − | − |
|  | 1 × 10$^6$ | ++ | ± | ++ | ± | − | ± |
|  | 1 × 10$^7$ | +++ | ±~+ | +++ | + | − | ± |

As obvious from Table 3, the P30 protein-detecting immunochromatographic test strip prepared in Example 5 of the present invention showed noticeable blacking for 1×10$^7$ CFU/mL of M129 strain and 1×10$^6$ CFU/mL of FH strain and showed clear blacking for 1×10$^6$ CFU/mL of M129 strain and 1×10$^5$ CFU/mL of FH strain.

In contrast, the conventional method showed clear blacking for 1×10$^7$ CFU/mL or more of M129 strain and 1×10$^7$ CFU/mL of FH strain.

As obvious from the results shown in Table 3, the results of comparison of the bacterial concentrations of test samples at which the same degree of blacking was shown demonstrated that the detection sensitivity of the P30 protein-detecting immunochromatographic test strip prepared in Example 5 of the present invention was about 100-times higher for M129 strains and also 100-times higher for FH strains, compared with the sensitivity of the P1 protein-detecting immunochromatographic test strip. In addition, the conventional method showed a slight cross-reactivity with *Mycoplasma genitalium*, and non-specific blacking was observed. No cross-reactivity was observed on the P30 protein-detecting immunochromatographic test strip of the present invention.

The results described above demonstrated that the P30 protein-detecting immunochromatographic test strip using the anti-P30 antibody of the present invention can detect *Mycoplasma pneumoniae* with high sensitivity and specificity.

Example 7

Detection of *Mycoplasma pneumoniae* From Throat Swab

Throat swabs were collected from 20 patients clinically suspected of infection with *Mycoplasma pneumoniae* with sterilized cotton swabs. The throat swabs were each verified as to whether *Mycoplasma pneumoniae* was present in the throat swab or not by the nucleic acid amplification test reported by National Institute of Infectious Diseases, Japan. Based on the results, sixteen samples (positive samples) in which the presence of *Mycoplasma pneumoniae* was confirmed and four samples (negative samples) in which the gene was not detected were selected from the collected throat swabs. The selected throat swabs were prepared as test samples. The test samples were subjected to detection of *Mycoplasma pneumoniae* using the P30 protein-detecting immunochromatographic test strip of the present invention. A commercially available reagent detecting P1 protein of *Mycoplasma pneumoniae* was used as a conventional method.

The test sample (100 μL) was dropwise added with a micropipette to the sample receiving member 5 of the immunochromatographic test strip prepared in Example 5 for chromatographic development by being left to stand at room temperature for 15 minutes. The complex of the antigen and the platinum-gold colloid-labeled antibody captured by the capturing zone 31 was observed with the naked eye to determine the result. The captured amount was determined by evaluating the degree of blacking, which is proportional to the amount, with the naked eye and classified into the following five stages: − (no blacking), ± (slight blacking), + (clear blacking), ++ (noticeable blacking), and +++ (extremely noticeable blacking). Table 4 shows the results of the test.

TABLE 4

| Sample No. | Present invention | Conventional method | Nucleic acid amplification test (PCR method) |
|---|---|---|---|
| 1 | ++ | + | + |
| 2 | ++ | + | + |
| 3 | +++ | + | + |
| 4 | ++ | ± | + |
| 5 | ++ | ± | + |
| 6 | + | ± | + |
| 7 | − | ± | − |
| 8 | − | ± | − |
| 9 | ± | − | + |
| 10 | ++ | + | + |
| 11 | − | − | + |
| 12 | + | ± | + |
| 13 | + | ± | + |
| 14 | − | − | − |
| 15 | ± | − | + |
| 16 | + | − | + |
| 17 | ± | − | + |
| 18 | − | − | − |
| 19 | + | ± | + |
| 20 | + | ± | + |

As obvious from Table 4, the comparison between the detection method of the present invention and the nucleic acid amplification test shows that the detection method of the present invention exhibited the high concordance rate, namely, a positive concordance rate of 93.8%, a negative concordance rate of 100.0%, and a total concordance rate of 95.0%, confirming that the detection method of the present invention can perform the detection with an accuracy equivalent to the nucleic acid amplification test. It is also shown that the detection method of the present invention is a detection method having high detection sensitivity and specificity, compared with the conventional method.

From the above results, it was confirmed that the immunochromatographic test strip of the present invention can detect *Mycoplasma pneumoniae* from throat swabs with high sensitivity and high accuracy.

INDUSTRIAL APPLICABILITY

The present invention provides a method and a kit for detecting *Mycoplasma pneumoniae*, comprising an immunoassay using an antibody recognizing a specific epitope of P30 protein of *Mycoplasma pneumoniae*, and makes it possible to rapidly and specifically diagnose infection with *Mycoplasma pneumoniae* without need of any specialized equipment or skill, compared with the conventional method.

DESCRIPTION OF SYMBOLS

1 Adhesive sheet
2 Impregnated member
3 Membrane carrier
31 Capturing zone
32 Control capturing zone
4 Absorbing member
5 Sample receiving member

The invention claimed is:

1. An immunochromatographic assay for detecting *Mycoplasma pneumoniae*, comprising:
    providing a membrane carrier having a capturing zone that is formed by previously immobilizing a first antibody against P30 protein of *Mycoplasma pneumoniae* at a predetermined position;
    chromatographically developing a liquid mixture in the membrane carrier toward the capturing zone, said liquid mixture containing a second antibody against the P30 protein and a predetermined amount of a test sample, whereby a complex of an antigen contained in the test sample and the second antibody is captured by the capturing zone when the P30 protein is contained in the test sample,
    wherein
        the test sample is a biological sample, and
        the first and second antibodies, which may be the same or different from each other, are each a monoclonal antibody against an epitope of P30 protein located in any one of amino acid sequences of SEQ ID NOS: 3 to 5, and having a sensitivity for detecting *Mycoplasma pneumoniae* strain M129 in a culture having a concentration of $1\times10^6$ CFU/ml of the M129 strain and detecting *Mycoplasma pneumoniae* strain FH in a culture having a concentration of $1\times10^6$ CFU/mL of the FH strain, as measured by the aforementioned immunochromatographic assay for detecting *Mycoplasma pneumoniae*.

2. The immunochromatographic assay according to claim 1, wherein the second antibody is labeled with any one of a colloidal metal, a latex, and a fluorescent substance.

3. The immunochromatographic assay according to claim 1, wherein the membrane carrier is a nitrocellulose membrane.

4. The immunochromatographic assay according to claim 1, wherein said monoclonal antibody shows little cross-reactivity with *Mycoplasma genitalium*.

5. The immunochromatographic assay according to 1, wherein said monoclonal antibody shows no cross-reactivity with *Mycoplasma genitalium*.

6. The immunochromatographic assay according to claim 1, wherein said monoclonal antibody is a mouse monoclonal antibody.

7. The immunochromatographic assay according to claim 1, wherein said monoclonal antibody is one obtained by immunizing an animal with a protein comprising an amino acid sequence of SEQ ID NO: 2 to obtain hybridomas, and selecting therefrom a hybridoma producing a monoclonal antibody specifically reacting with a polypeptide having an amino acid sequence of any one of SEQ ID NOS: 3 to 5.

8. The immunochromatographic assay according to claim 7, wherein said monoclonal antibody shows substantially no reaction with a polypeptide having an amino acid sequence of SEQ ID NO: 6 or 7.

* * * * *